United States Patent [19]

Maher, Jr. et al.

[11] 4,037,003

[45] July 19, 1977

[54] METHOD FOR BLOOD FILM PREPARATION

[75] Inventors: Francis William Maher, Jr., Milford; Vladimir Valentine Pirc, Norwalk, both of Conn.

[73] Assignee: The Perkin-Elmer Corporation, Norwalk, Conn.

[21] Appl. No.: 758,998

[22] Filed: Jan. 13, 1977

Related U.S. Application Data

[62] Division of Ser. No. 669,015, March 22, 1976, Pat. No. 4,016,828.

[51] Int. Cl.² .................... A01N 1/02; B05C 11/02; G01N 1/28
[52] U.S. Cl. .................................. 427/2; 427/240
[58] Field of Search .................. 427/2, 6, 8, 9, 10, 427/240, 241, 346; 118/2, 7, 8, 12, 52, 53, 56; 34/58; 233/46, 14 R; 68/23.5; 134/33

[56] References Cited

U.S. PATENT DOCUMENTS

| 2,412,099 | 12/1946 | Sender | 233/46 X |
|---|---|---|---|
| 2,580,131 | 12/1951 | Rowell | 118/52 X |
| 2,941,499 | 6/1960 | Gutzmer | 118/52 X |
| 2,952,557 | 9/1960 | Charron | 118/52 X |
| 3,280,792 | 10/1966 | Heyde | 118/52 |
| 3,705,048 | 12/1972 | Staunton | 118/52 X |
| 3,906,890 | 9/1975 | Amos et al. | 118/6 |

*Primary Examiner*—Morris Kaplan
*Attorney, Agent, or Firm*—S. A. Giarratana; F. L. Masselle; J. D. Crane

[57] ABSTRACT

Sample preparation apparatus for forming a thin layer of diluted blood specimen on a substrate by centrifugal force includes a sample probe having coaxial blood and diluent conduits coupled to respective reversibly drivable peristaltic pumps having forward operation intakes connected to a diluent supply. A one-way clutch limits the diluent pump to forward operation and the pumps are geared to produce a blood-to-diluent displacement ratio of 2:1. A substrate holder is mounted on a carriage for selective insertion into and removal from a sealed centrifuge chamber in which it is spun at a high angular rate by a drive motor. Means are provided to form a curtain of flowing liquid within the chamber surrounding the spinning substrate to collect spun-off blood particles and aerosol. The liquid forming the curtain is drained by an exhaust pump which operates after spinning has ceased so as to create a partial vacuum for draining off residual aerosol prior to unsealing the centrifuge chamber.

9 Claims, 11 Drawing Figures

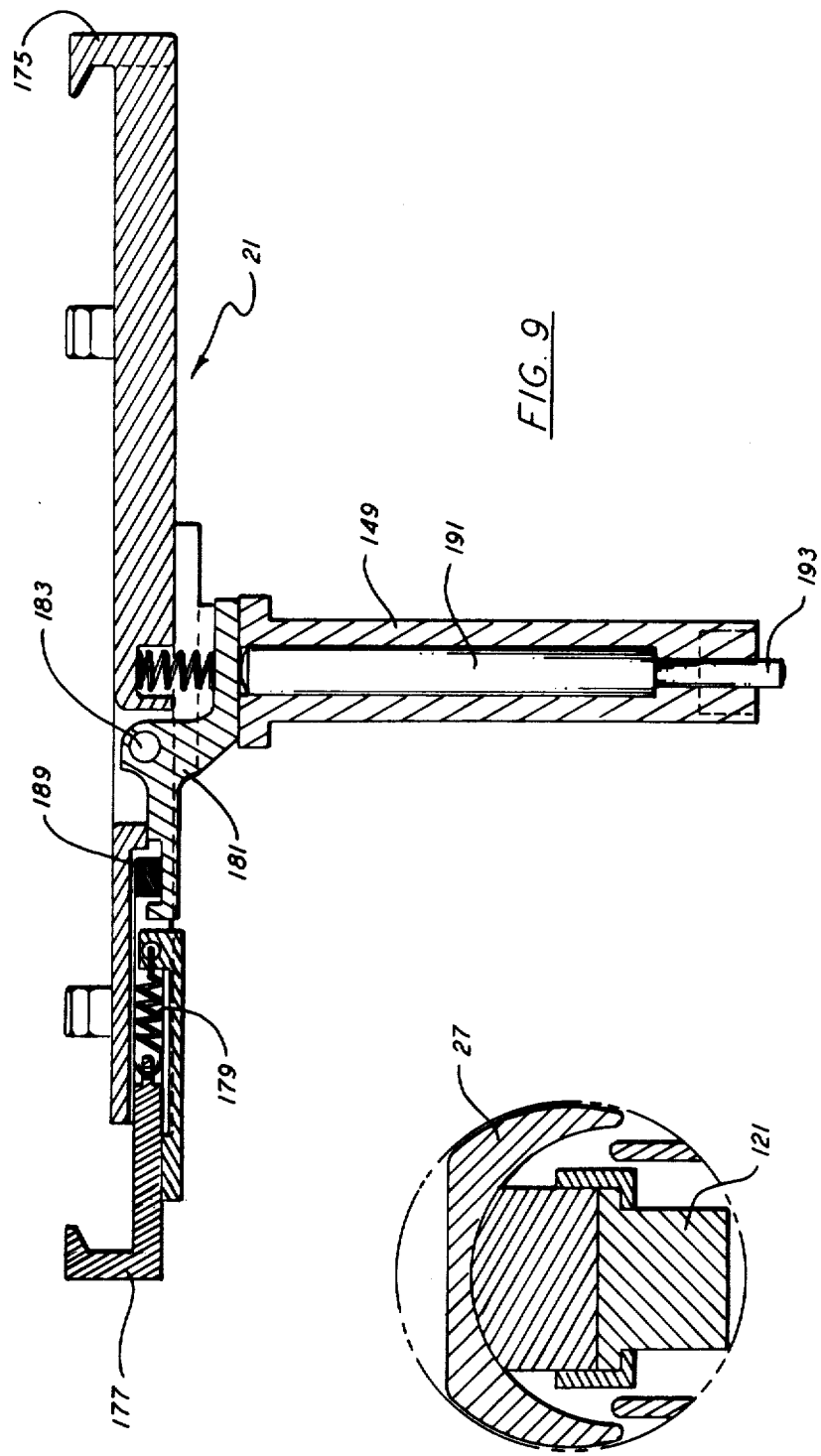

METHOD FOR BLOOD FILM PREPARATION

This is a division of application Ser. No. 669,015, filed Mar. 22, 1976, now Pat. No. 4,016,828.

BACKGROUND OF THE INVENTION

This invention relates generally to a clinical method for medical diagnosis and, more particularly, to an improved method for the preparation of blood sample films or "smears" on microscope slides or similar substrates. While applicable to all techniques for evaluation of the resulting smears, the method and apparatus are especially adapted for use in connection with automated blood cell analysis using computerized pattern recognition systems.

The traditional method of preparing blood smears on microscope slides for evaluation by physicians or medical technicians consists of placing a small quantity of the blood specimen on a microscope slide and then manually wiping the blood across the slide with the edge of another slide or a cover glass. While reasonably satisfactory for the preparation of smears for microscopic examination by skilled technicians or physicians, the obvious variations in results from slide to slide inherent in such a manual technique obviously renders it wholly unsuitable to preparation of slides for evaluation by automated pattern recognition apparatus.

An early attempt to achieve a high degree of control and uniformity in the preparation of blood smears is described in U.S. Pat. No. 3,577,267 granted to K. Preston, Jr. et al. on May 4, 1971. The method and apparatus proposed by Preston et al. involves placing a small specimen on a substrate and then spinning the substrate at high speeds, thus utilizing centrifugal force to form an evenly distributed thin layer of blood on the substrate surface with a minimum of disturbance to blood cell morphology. This involves rapid acceleration of the substrate and spinning at high speeds in the range of from 4,000 to 10,000 rpm according to the Preston et al patent. Consequently, the greater portion of the original specimen is spun off the slide, much of it in the form of aerosol. A shield is provided around the spinner to prevent widespread scattering of the spun-off blood but does little or nothing to prevent aerosol from entering the atmosphere of the laboratory.

Inasmuch as some of the blood specimens routinely handled in hospital and private clinical laboratories contain pathogenic organisms, the use of spinners and the resultant dispersal of aerosol constitutes a health hazard for clinical personnel, exposure to hepatitis virus being a particular problem.

The containment of aerosol by disposing the spinner in an enclosed chamber such as that shown in U.S. Pat. No. 3,705,048 to J.J.J. Staunton, represents a partial solution only because the aerosol persists within the chamber and eventually escapes into the atmosphere when the cover is opened.

Another problem encountered in the utilization of centrifuges to prepare blood smears is the variation in hematocrit from specimen to specimen which makes it necessary to adjust the spinning parameters (e.g., acceleration, speed and spinning time) in order to obtain a degree of uniformity in the resulting smear. In this connection, reference may be had to U.S. Pat. No. 3,906,890 to Amos et al. describing a blood smear centrifuge in which spinning time is automatically adjusted in accordance with the hematocrit of the specimen. Obviously, it would be preferably if the spinning parameters could be the same for all or at least the vast majority of blood specimens and, to this end, it has been suggested (J. W. Bacus, Erythrocyte Morphology and Centrifugal "Spinner" Blood Film Preparations, J. of Histochemistry and Cytochemistry, Vol. 22, No. 7, pp. 506-516) that it would be desirable to adjust the hematocrit in order to permit slides to be spun at the same speed and for the same time. Adjustment of the hematocrit may be accomplished by dilution of the blood specimen with physiological saline. To avoid the necessity of adding sample dilution to the procedures performed by the operator and to ensure uniformity in the proportions of sample and diluent, it is highly desirable that the dilution be carried out automatically. It is to the automatic accomplishment of dilution as well as the prevention of atmospheric contamination with aerosol that the present invention is addressed. It is the basic general object of the invention to provide a blood smear preparation method which overcomes or mitigates problems of the prior art as outlined hereinabove.

A more specific object is the provision of a sample preparation method for preparing blood smears on substrates which are particularly suitable for evaluation by computer operated pattern recognition apparatus or the like which produces smears of high uniformity and reproducibility.

A further object is the provision of a method in accordance with the preceding objects which effects blood specimen dilution and spinning essentially without operator intervention and which effects the formation of a blood smear by centrifugal action without the attendant hazard of dispersing possibly pathogenic blood particles and aerosol into the atmosphere.

SUMMARY OF THE INVENTION

To the accomplishment of the foregoing objects and the attainment of further objects and advantages which will become apparent as this description proceeds, the invention contemplates a method of blood smear preparation in which a blood specimen is deposited on a planar substrate which is then spun at a high angular rate about an axis normal to its plane while the substrate is surrounded by a flowing curtain of liquid positioned to intercept and collect blood particles and aerosols spun off the substrate.

The invention is embodied in apparatus consisting of two basic components: (1) a sample aspirating and diluting probe which picks up a specimen quantity of blood, automatically mixes it with diluent in a fixed proportion, and then, on signal, discharges the diluted specimen and (2) a substrate spinner or centrifuge which, when operative, is completely enclosed in a sealed housing to prevent contamination of the surrounding area by blood particles or aerosol generated as a result of centrifuge operation. Means are provided to form a curtain of flowing liquid within the enclosure surrounding the substrate while spinning to intercept and collect blood particles and aerosol. The liquid forming the curtain is then directed to a drain. Discharge of the curtain-forming liquid to drain is accomplished by positive exhaust pumping which is continued after rotation of the centrifuge has ceased in order to create a partial vacuum within the enclosure and thus ensure the removal of residual aerosol prior to opening of the enclosure.

In accordance with particular additional features of the invention, the centrifuge includes a substrate holder mounted on a carriage which may be withdrawn or retracted from the enclosure to permit insertion of a substrate. Advancing the carriage into the housing automatically effects locking of the substrate in the holder and sealing of the centrifuge enclosure; automatically effects coupling of a drive motor to the substrate holder; and locks the carriage in the enclosure to prevent its retraction during the spinning cycle.

The probe is employed by the operator to deposit a metered quantity of diluted blood onto the substrate, preferably after it is loaded into the substrate holder. The internal surfaces of the probe which have been in contact with the blood specimen are cleansed by discharge of diluent subsequent to depositing the sample on the substrate and the external surfaces cleansed during the operation of the centrifuge by a spray of liquid from the same source as that forming the liquid curtain.

Through these various features, a safe, efficient, reliable and easy to operate system is provided for the preparation of blood sample smears.

BRIEF DESCRIPTION OF THE DRAWINGS

FIG. 8 is a section on line 8—8 of FIG. 7;

FIG. 9 is a sectional view of the substrate holder portion of the apparatus as shown in FIG. 7, taken on the spin axis;

DETAILED DESCRIPTION OF THE PREFERRED EMBODIMENT

Figure 1:
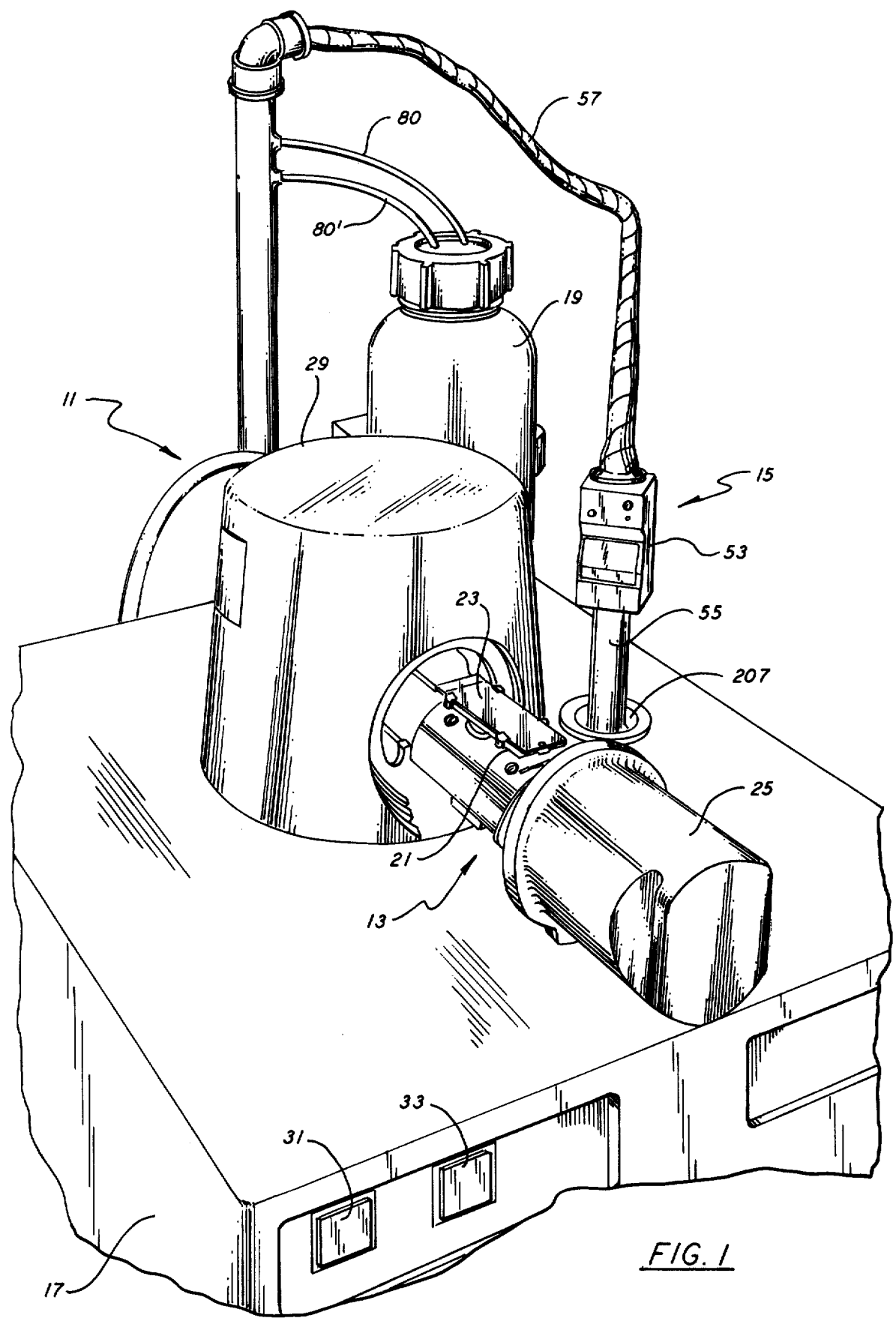
FIG. 1 is a perspective view of the blood film preparation apparatus of the present invention.

Referring now to the drawings and first in particular to FIG. 1, there is shown and indicated generally as 11, a blood film preparation apparatus in accordance with the present invention. As already mentioned, there are two major components of the apparatus, a centrifuge assembly 13 and a sampling probe 15. Preferably, both are mounted on a self-contained, easily movable cart unit 17. Also appearing in FIG. 1 is a diluent container 19, which supplies diluent (usually physiological saline) to probe 15, as well as associated electrical conductors and liquid conduits described in greater detail hereinbelow. Centrifuge assembly 13 includes a substrate holder 21 on which is disposed a substrate 23, e.g., a standard microscope slide. Substrate holder 21 is mounted on a carriage 27 which rides on tracks extending into a centrifuge chamber defined by an enclosure 29. A handle member 25 on the outer end of carriage 27 enables the carriage to be advanced into enclosure 29 or retracted therefrom in a manner which will become apparent as this description proceeds. In FIG. 1, substrate holder/carriage assembly 21, 27 is illustrated in the retracted or open position, i.e., ready to permit insertion or removal of a substrate.

At this juncture, the basic operational sequence of the apparatus will be related as a preface to, and to facilitate understanding of, the structural aspects of the invention. The operator, after turning on the apparatus and getting an indication on an indicator 31 that the system is ready for operation (possibly after purging the system with a rinsing liquid, such as water, by operating a purge button 33) aspirates a blood specimen by inserting the tip of probe 15 into the blood sample and pressing a control switch 35 on the handle of the probe. This causes aspiration of a predetermined quantity of the blood sample into the probe wherein it is mixed with a diluent in a manner to be described presently. Thereupon, the operator places the tip of the probe over substrate 23 and actuates control switch 35 once again. This causes discharge of a metered quantity of the diluted blood sample onto the substrate. The operator then moves the substrate holder/carriage assembly into chamber 29, by pushing on handle 25, and concomitantly automatically initiates operation of the centrifuge. Movement of the holder/carriage into chamber 29 also completes closure of and seals the chamber.

Figure 2:
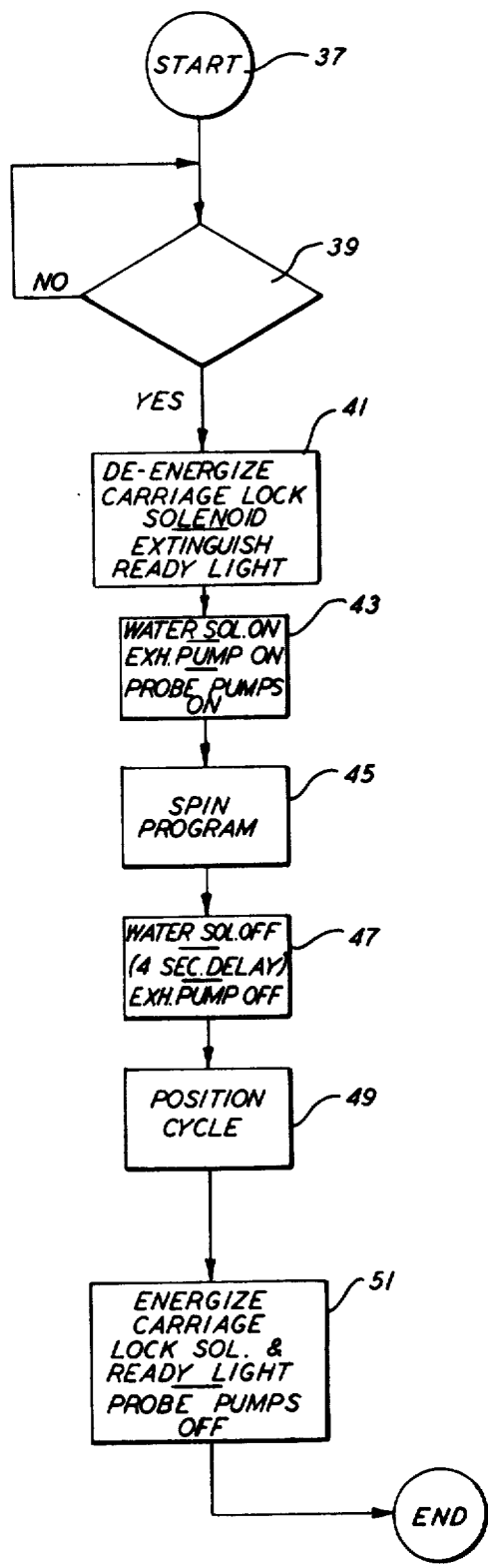
FIG. 2 is a flow chart of the overall operation of the apparatus of FIG. 1.

The remainder of the operating cycle can best be appreciated by reference to the flow diagram shown in FIG. 2. From a start block 37 at the beginning of the program, a signal flows to a decision block 39 where a start check is made to determine if the substrate holder/carriage assembly has been moved into the centrifuge chamber. If negative, recycling occurs; if affirmative, indicating that the substrate holder/carriage is in the closed position, the substrate is locked in place so that rotation can safely begin as represented by first instruction block 41. This condition is visually represented to the operator by extinguishment of a "ready light."

The next instruction block, 43, represents the turn-on of the fluid systems associated with the apparatus and more specifically the inlet valve and exhaust or drain pump for the liquid forming the curtain around the spinning substrate and the pump for the sample diluent. In this connection, the liquid forming the curtain is normally water and may be referred to as such hereinafter. Accordingly, the explanatory legend beside the block 43 in FIG. 2 refers to the "water solenoid" and "water drain pump."

The next instruction block 45, controls the spin program, viz., the initiation, speed regulation, and termination of the centrifuge operation. It should be noted that spinning is not initiated until after the water forming the protective curtain has been turned on.

When the spinning cycle is completed and the centrifuge stopped, the water curtain is turned off by turning of the water solenoid valve and, after a 4-second delay, exhaust pump operation is terminated as indicated by instruction block 47. Thereafter, the centrifuge motor is positioned as instructed by block 49 to permit the engagement and disengagement of coupling between the substrate holder and the motor. Block 51 is entered, the ready reset, rotate set to 0 to lock the motor in position, the lock solenoid opened to permit withdrawal of the substrate and the diluter pumps turned off. During the time that the water valve is open, water is provided not only to the inside of the enclosure 29 where it forms a curtain to collect and carry away spun-off blood particles and aerosol, but is also directed to cleanse the external portion of the probe.

Figure 3:
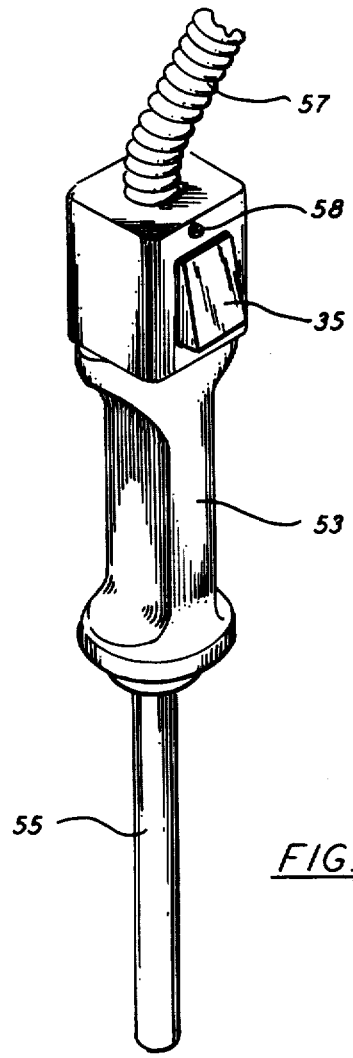
FIG. 3 is a perspective view of the sample aspirating-/diluting probe of the apparatus of FIG. 1.

FIG. 3 is a perspective view of the probe 15 of FIG. 1. As illustrated, it includes a grip portion 53 and a shank portion 55, the tip of which is immersed in a blood sample to aspirate a specimen to be used on the substrate. A flexible tubular sheath 57, connected to the grip end of the probe, houses tubing for the diluent and electrical control conductors. Adjacent grip 53 is the switch or sequence button 35 which controls the probe functions involved in aspirating blood and expelling it in a diluted condition onto the substrate. Above button 35 is an LED display 58 for indicating the status of the probe.

Figure 4:
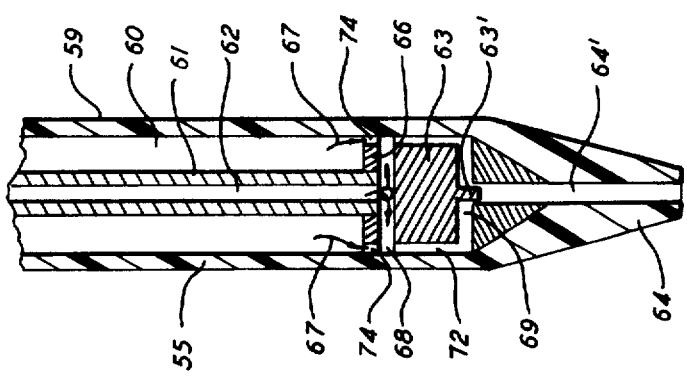
FIG. 4 is a longitudinal sectional view of the tip portion of the probe of FIG. 3.

In order to achieve satisfactory results in the preparation of blood specimen films in accordance with the present invention, it is essential that mixing of blood and diluent by the probe be carried out in an effective manner. A cross-section of the probe construction which accomplishes such mixing is shown in FIG. 4 which illustrates a lower segment of the shank portion 55. While only partially illustrated, substantially the entire shank of the probe is made up of coaxially disposed hollow tubular members 59 and 61. The inner member 61, which defines a conduit 62 for the aspiration of a blood specimen preferably is made of stainless steel; the outer member 59 which defines a diluent passage 60 surrounding the inner member preferably is fabricated of Teflon or the like.

The lower end of outer member 59 is conically tapered to form a small diameter tip 64 which is easily inserted into a blood sample cup to aspirate a specimen and facilitates its subsequent deposit, in diluted form, on the substrate.

Inner tubular member 61 terminates at a distance from the tapered portion 64 of outer member 59 in communication with a mixing region or chamber there located. The mixing chamber, formed by the coaction of individual or integral mechanical elements 63, 66, the physical details of which are not material, takes the form of a thin discoid upper portion 68 and an annular lower portion 69 interconnected by a plurality of axial passages 72. Upper portion 68 of the chamber is in direct flow communication with diluent conduit 60 via a plurality of ports 74 and lower chamber portion 69 communicates with an axial duct 64' opening at the external tip of the probe. A cylindrical projection 63' extends from element 63 into the inner end of duct 64' with a small clearance, e.g., to create an annular flow restriction at that point which aids in the mixing of blood and diluent and breaks up any clots which might form.

Conduit 60 is filled with diluent and is in communication with a diluent pump as hereinafter described; similarly, conduit 62, normally also filled with diluent, is in communication with a blood sample pump. During aspiration of a blood specimen, only the sample pump is operative and blood is drawn through tip duct 64' and the mixing chamber into the lower end portion of conduit 62. Thereafter, when the diluted specimen is to be deposited on the substrate, both the diluent and sample pumps are operated so that blood and diluent are simultaneously discharged into the mixing chamber. As indicated by the arrows in FIG. 4, blood follows the path represented by arrow 65 and diluent the path represented by arrows 67. The two flows merge in the upper portion 68 of the mixing chamber, pass through axial passages 72 and into the lower portion 69 of the mixing chamber and then through the restricted annular orifice into tip duct 64'.

Figure 5:
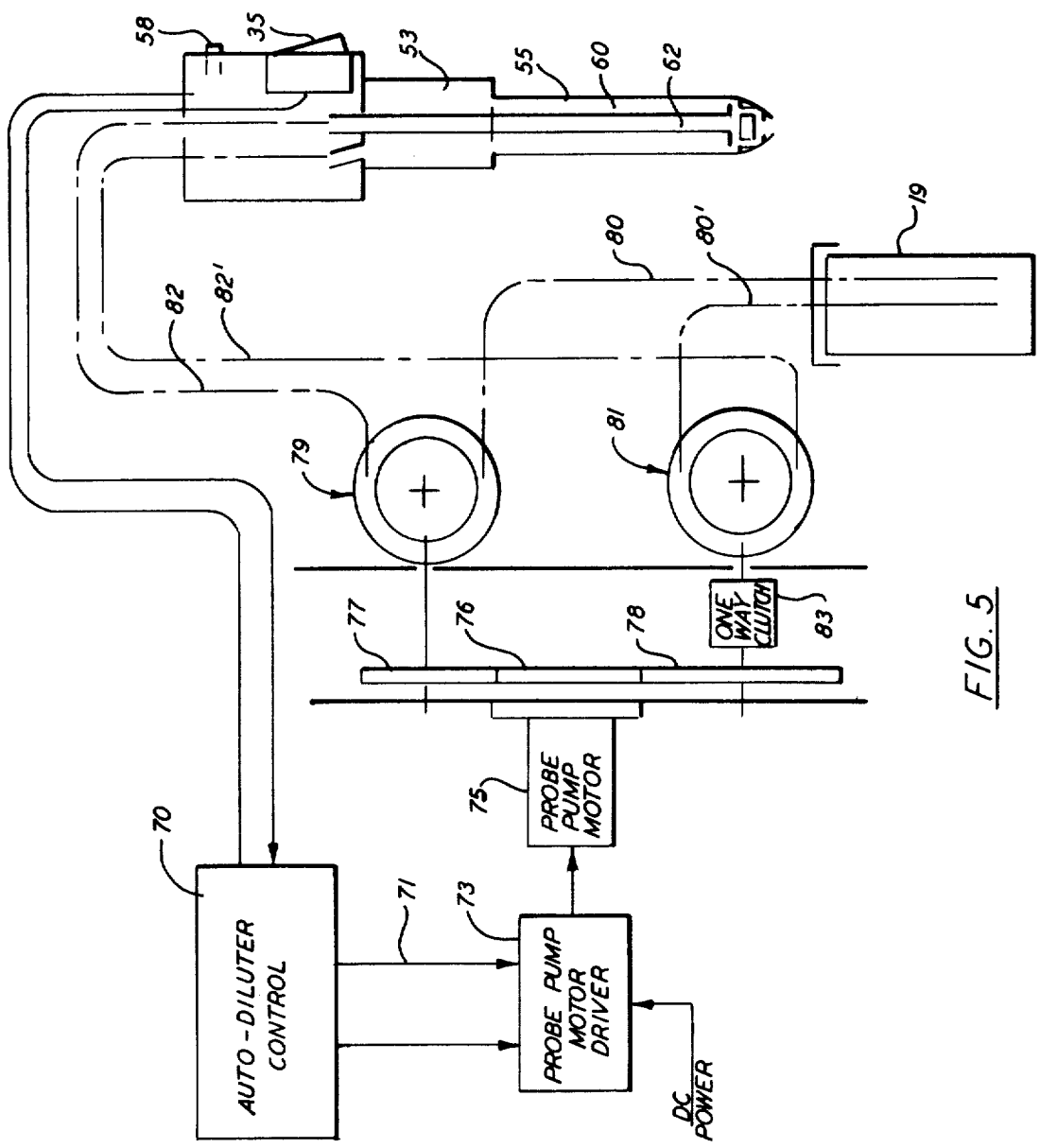
FIG. 5 is a block diagram of the pumping and control system associated with the probe of FIG. 4.

Probe 15, with the structure just described shown schematically, is illustrated in FIG. 5 in conjunction with its pumps and associated controls. As indicated, push button 35 is coupled to an autodiluter control block 70 with a voltage therefrom supplied back to LED display element 58. Control block 70, described in greater detail hereinbelow, upon receipt of a signal from push button 35 issues a reverse signal on line 71 to the pump motor driver 73. This causes a voltage to be supplied to a small, e.g., 24 volt d.c., reversible motor 75 having on its shaft a gear 76 meshing with grears 77 and 78. Gear 77 has the same number of teeth as gear 76, e.g., 27 teeth, and gear 78 twice that number. Gear 77 is fixed on the shaft of blood sample pump 79 and gear 78 coupled to a diluent pump 81 through a one-way clutch 83. The one-way clutch is oriented to permit diluent pump 81 to run only in the forward direction; nevertheless, both pumps are reversible in operation and, in order to achieve the high precision volume displacement required, peristaltic-type pumps are preferred. Accordingly, while both pumps have inlet and outlet flow passages or ports, the function of the flow passages of the sample pump depends on the direction of operation, thus, the passage functioning as a discharge when the sample pump is running forwardly, becomes an intake passage for aspiration of blood when the pump is reversed.

Both pumps have coupled to thier forward-running inlet side tubes 80, 80' which lead to the diluent supply 19. The forward running outputs of the sample and diluent pumps 79 and 81 are coupled through tubing 82, 82' to sample and diluent conduits, respectively, or probe 35. When motor 75 is operating in reverse, pump 79 runs in reverse to aspirate blood in the manner described above. When the probe is positioned over the substrate, push button 35 is operated again and autodiluter control system 70 causes motor driver 73 to dispense the sample. This involves a momentary excitation of motor 75 in the reverse direction so that all of the blood specimen in the mixing chamber is drawn completely into conduit 62 and then in the forward direction causing, because of the different gear ratio, two parts of blood to be mixed with one part of diluent and dispensed by the probe.

The operation of motor 75 is controlled as will be described presently so that only the desired volume of diluted blood is deposited on the substrate. In the preferred embodiment, approximately 190 microliters of sample are drawn in. When the button is pushed a second time, the reverse drive is energized briefly as explained above, e.g., approximately 80 milliseconds, to clear the mixing chamber. After a 420-second delay motor 75 is energized in the forward direction to dispense approximately 125 microliters of blood and 62.5 microliters of diluent for an approximate total quantity of 187.5 microliters of the mixture being deposited on the substrate. Thereafter, probe 15 is placed on its holder.

Figure 6:
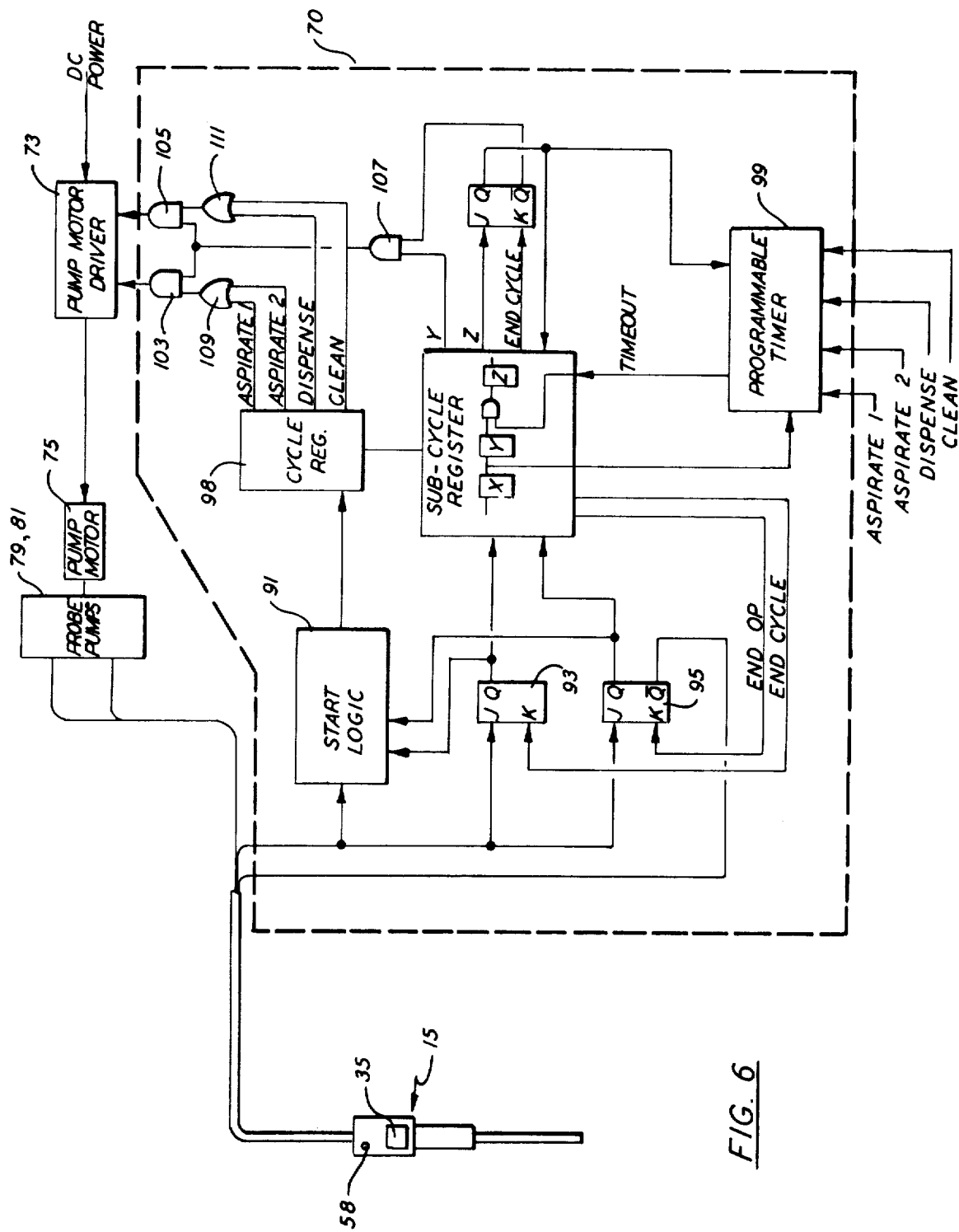
FIG. 6 is block-logic diagram of the control system of FIG. 5.

FIG. 6 is a block-logic diagram of the control circuit 70 of FIG. 5 including, for ease of reference, a diagrammatic representation of probe 15 and its push button 35 and LED indicator 58. Also included are pumps 79 and 81 with their drive motor 75 and the motor driver 73. The remainder of the elements, which are enclosed within dashed lines, comprise control system 70 which is made up of logic circuit building blocks such as Texas Instruments' 7400 and 9300 series units. The logic is not shown in complete detail since the design will be evident to those skilled in the art.

The basic elements include a start logic block 91, a cycle flag flip-flop 93, a wait flip-flop 95, a subcycle register 97, a cycle register 98, a programmable timer 99 and delay flag 101. The output from the various modules is coupled through a number of gates. The forward and reverse inputs into pump motor driver 73 is through AND gates 103 and 105, respectively. These obtain an enabling input from an AND gate 107 and obtain their second inputs respectively from OR gates 109 and 111.

Programmable timer 99 can be present with time settings as indicated by the inputs thereto. As noted above, the probe first aspirates a blood sample and thereafter continues aspiration to draw blood out of the mixing chamber. The probe then dispenses the diluted specimen and, after being placed back in its holder, is cleansed. The time of occurrence and duration of each of these steps (e.g., the times mentioned for aspirating and dispensing) are set into the programmable timer 99.

Upon the first depression of the button 35, inputs are provided to the start logic 91 and to the flip-flops 93 and 95. The start logic provides an output to the cycle register 98 resetting it to the "aspirate 1" position. Flip-flops 93 and 95 are set and provide inputs to subcycle register 97. The output flip-flop of 95 is also coupled to the LED display 58 to indicate to the operator that a cycle is in progress. Subcycle register 97 provides an output to the programmable timer causing it to generate an output representing the desired time for the first aspiration. Register 97 also provides an output on the line labeled "Y" to the AND gate 107. At this point, delay flag flip-flop 101 is reset so its Q output is a 1. AND gate 107 is now enabled and will have a 1 output which is provided to AND gates 103 and 105. Since cycle register 98 is in the "aspirate 1" position, there will be a 1 at the input to OR gate 109 and thus a 1 at its output. As a result, AND gate 103 has two 1 inputs and will provide a 1 output to pump motor driver 73 causing motor 75 to run in reverse.

At the end of the "time-out" signal from programmable timer 99, flip-flop 101 is reset, disabling AND gate 107 which will, in turn, disable AND gate 103 stopping the motor. At the same time, an output will be provided resetting cycle flag flip-flop 93. Subcycle register 97 will provide a shift output to shift cycle register 98 to "aspirate 2." Once the operator has positioned the probe over the substrate and again depresses button 35, the cycle flag will again be set causing the subcycle register to cause the programmable timer to output the time for "aspirate 2." In the manner indicated above, this aspiration will be carried out, the OR gate 109 now obtaining its input from "aspirate 2." At the end of that time, subcycle register 97 will provide a shift output to cycle register 98 resulting in the "dispense" output (which is an input to OR gate 111). Programmable timer 99 will also be stepped to the next output, i.e., the "dispense" output. Now, in the manner described above, AND gate 107 will be enabled for the preset time enabling AND gates 103 and 105. For this step, there are no 1 inputs at OR gate 109 and thus, the motor will drive in reverse. However, one of the inputs to OR gate 111 is present so that AND gate 105 will have two 1 inputs and will provide a forward signal to the driver. This will cause the motor to drive forward in the manner described above to deposit the diluted sample on the slide.

Thereafter, subcycle register 97 will shift cycle register 98 to the "clean" output simultaneously shifting programmable timer 99 to that output. After a delay sufficient to permit the operator to place the probe back in its holder, the "clean" cycle will be carried out in the manner described above with the pumps forcing diluent through both diluent and sample conduits of the probe.

At the end of this time, the "end cycle" signal from the subcycle register along with the "end op" signal will be provided, resetting both flip-flops 93 and 95. The LED display 58 will now indicate that a new cycle can be carried out. The outputs of flip-flops 93 and 95 are also provided as enabling inputs to start logic 91 so that only when flip-flops are reset, indicating a complete operating cycle has been accomplished, can the start logic become effective. In other words, pressing the button during a cycle will not have an effect (other than causing a sample to be dispensed once aspiration has taken place).

As indicated above, once the diluted blood specimen has been placed on the substrate, it is moved into the centrifuge chamber in enclosure 29 (FIG. 1) where it is then spun.

Figure 7:
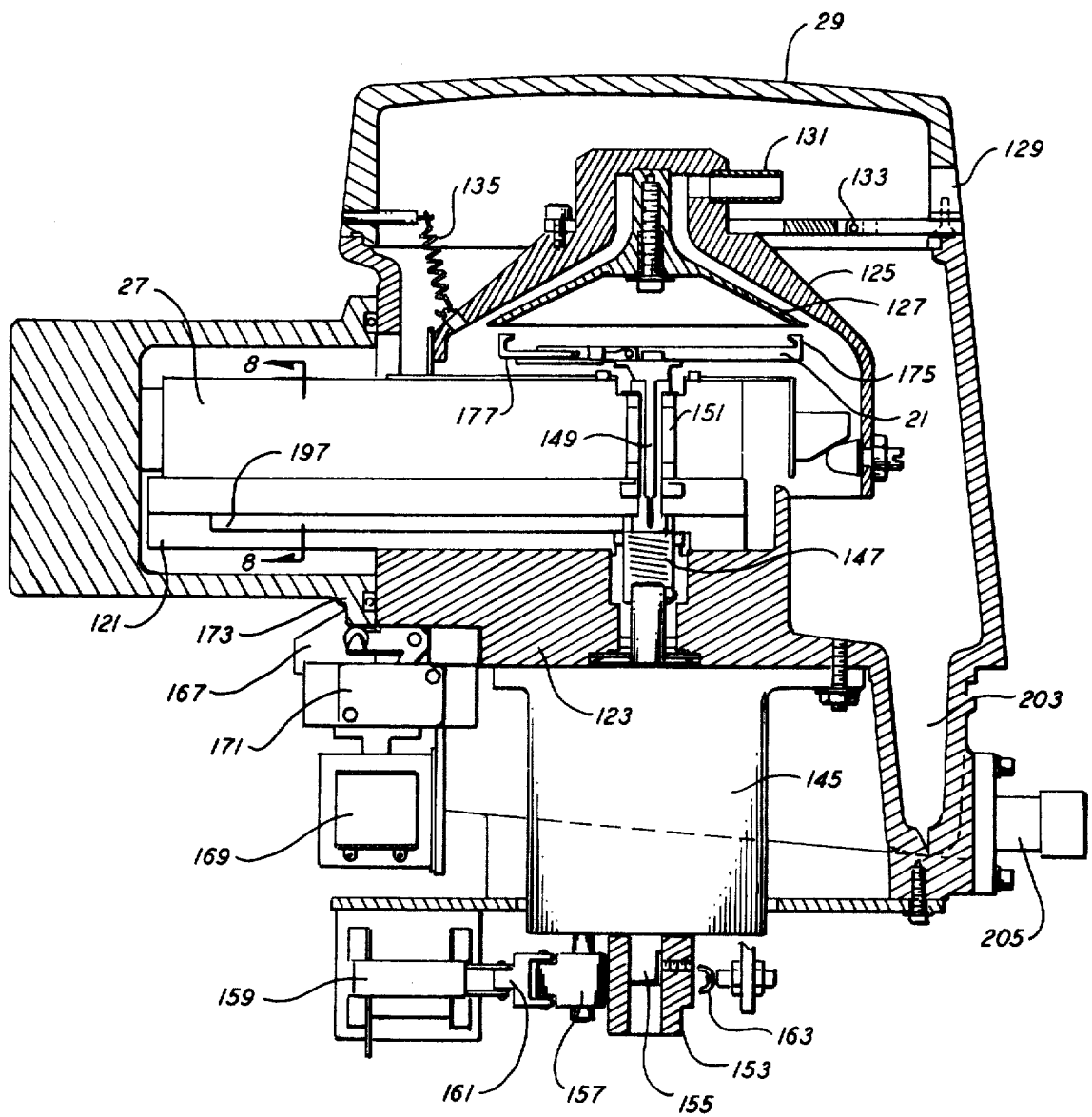
FIG. 7 is a sectional view of the centrifuge portion of FIG. 1, the section being taken in the plane of the spin axis.

As can be seen from FIGS. 7 and 8, carriage 27 for substrate holder 21 slides into and out of enclosure 29 on a track 121 bolted to a base 123 for the enclosure in any suitable and conventional fashion.

Within enclosure 29, above the area occupied by substrate holder 21 during spinning, is a water-curtain forming assembly, comprising a deflector 125 and a spreader 127. A water conduit enters enclosure 29 through an opening 129 and is joined to a coupling 131 passing through deflector 125 so as to feed water to the space between the deflector and spreader 127. The gap between the deflector and spreader is adjusted to about 0.002 to 0.003 inches so that when water is supplied to the area therebetween, a curtain of water forms around the periphery of the spinning substrate.

In order to permit insertion and removal of the substrate on holder 21, the assembly made up of the delector 125 and spreader 127 is pivoted about a point 133. A spring 135 biases the front of the assembly upward to provide clearance for the substrate and holder 21 when retracted. In the fully inserted position shown, a cam 137 acts on a stop 139 securely mounted to a depending annular flange 141 of the spreader to push the assembly into the position shown against the force of the spring 135. Slide holder 21 is rotated to carry out the spinning by a motor 143 secured to base 123 below the centrifuge chamber. The motor shaft protrudes vertically upwardly through a carbon seal 145 into a spring coupling 147 slotted to engage with a complementary projection on the end of a shaft 149 on which slide holder 21 is supported. Shaft 149, journalled in a bearing 151 in carriage member 27, is actually a dual (coaxial) shaft assembly as will be explained in the ensuing description relating to FIG. 9.

To ensure that centrifuge motor 145 always stops with the notch of coupling 147 properly aligned, a detent disc 153 is attached to the downwardly projecting lower shaft 155 of motor 143. Disc 153 contains a detent which is engaged by a detent mechanism 157 coupled to a solenoid 159 through a coupling 161. Detent mechanism 157 is biased toward detent disc 153 by means of a spring 163. When the centrifuge is spinning, solenoid 159 is energized to move the detent 157 away from the disc to permit free rotation. However, as the motor speed is slowed after completion of the spin cycle, solenoid 159 is de-energized so that the detent will snap into the notch of detent disc 153 and stop the motor at the proper position to permit insertion and retraction of carriage member 27 with the slide holder 21 thereon. Also provided is a microswitch (not shown) which is closed when the detent is in place to provide an indication that the motor is stopped so that power can be removed to stop rotation.

Locking of carriage member 27 in place within the centrifuge chamber is accomplished by a latch 167 operated by a solenoid 169 controlled by a microswitch 171. When handle 25 is pushed in, a flange 173 thereon closes microswitch 171 to de-energize solenoid 169 causing the latch 167 to move upwardly and thus prevent the handle from being pulled out until the end of the spinning cycle when, in a manner to be described presently, the solenoid will again be energized.

Substrate holder 21 and its shaft 149 are shown in greater detail in FIG. 9. At one end (right-hand as viewed in FIG. 9) of the substrate holder, is a fixed, notched substrate gripping member 175 for engagement of an edge of a substrate; at the opposite end of the holder is a movable gripping member 177 adapted to engage on the opposite end of the substrate. Movable member 177 can slide toward and away from fixed member 175 and is biased toward the fixed member by a spring 179 to secure a substrate on the holder. Motion away from the fixed member can occur, however, only when a detent lever 181 is pivoted about a pivot pin 183 so as to be clear of a portion 189 of slidable member 177. Detent lever 181 is pivoted by means of an inner shaft 191 coaxially slidably disposed within shaft 149 and having a portion 193 projecting from the lower end thereof. Detent lever 181 is biased into the engaging position shown on the drawing by means of a spring 195. Projecting end 193 is also shown on FIG. 7 and it can be seen from both FIGS. 7 and 9 that, by pushing upward on projecting end 193, lever 181 will be angularly displaced to permit movement of member 177 toward and away from fixed member 175.

When the substrate holder assembly is within the centrifuge chamber, as shown in FIG. 7, the detent mechanism is in the position shown in FIG. 9 and, as movement of member 177 is not possible, the substrate is held firmly during spinning. However, as handle 25 is pulled out to withdraw the slide holder as carriage member 27 nears the end of its travel, the projecting portion 193 of shaft 191 rides up on a ramp 197 attached to track 121 with the carriage in fully withdrawn position, shaft 191 is pushed upward causing the opposite end of lever 181 to be moved downward so that the substrate can be removed and a new substrate inserted by displacing gripping member 177 outwardly against the pressure of spring 179.

Figure 10:
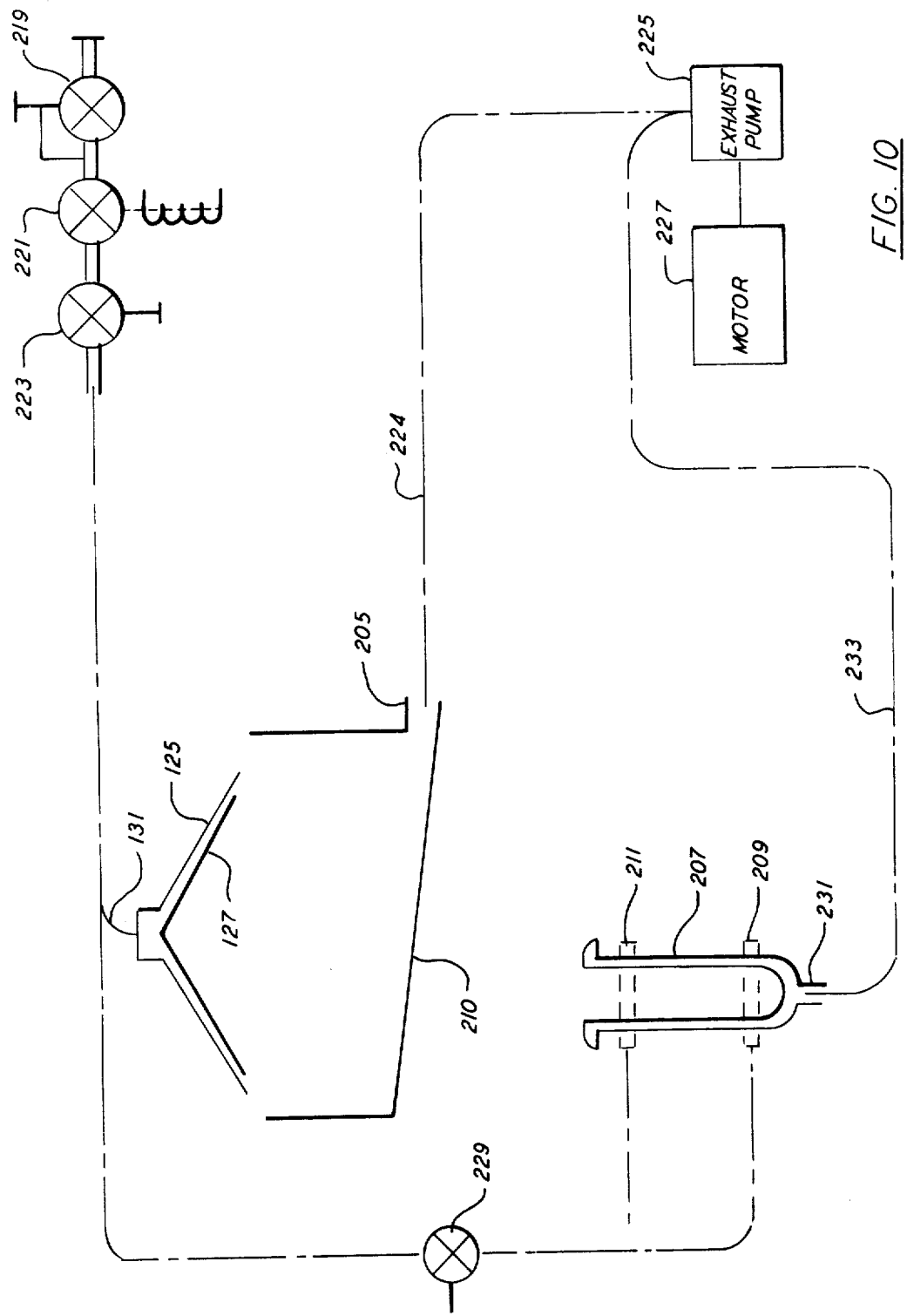
FIG. 10 is a plumbing diagram for the apparatus of FIG. 1 including the probe wash system.

FIG. 10 is a plumbing schematic illustrating the manner in which water is provided for the water curtain around the circumference of the spinning slide and also showing the manner in which the external portion of probe 15 is washed. Deflector assembly 125, 127 is schematically represented in FIG. 10, as is a bowl 201, which serves as a catch basis for water from the curtain. Bowl 201 is formed with a depression 203 (shown in FIG. 7) which connects via a coupling 205 to a drain or exhaust line 224. Also schematically shown in FIG. 10 is the previously mentioned holder 207 for probe 15 which includes two wash rings 209 and 211. Water from a spigot at line pressure is routed through a pressure regulating valve 219, a solenoid valve 221, and then to a flow valve 223. Typically, pressure regulator 219 is set for 50 psi. Water from flow valve 223 enters deflector assembly 125, 127 through inlet 131, details of which are shown in FIG. 17, and passes through to form the curtain of water around the spinning slide. Water is also supplied through a flow valve 229 to the wash rings 211 and 209 at a flow rate set so that the water level never rises about the upper wash ring 211. Wash water for the external part of the probe, along with diluent flushed through the probe in the manner described above, flows out through a drain 231 in the bottom of probe holder 207 via a drain line 233. Drain lines 224 and 233 are connected to an exhaust pump 225 driven by a motor 227. As indicated above, in connection with FIG. 2, exhaust pump 225 continues to run after the solenoid valve for the water supplying curtain is turned off. Inasmuch as the centrifuge chamber is sealed by movement of the slide holder carriage into the spin position, forced drainage creates a partial vacuum within the chamber to draw off residual aerosol before it is opened by retraction of the spinner assembly.

Figure 11:
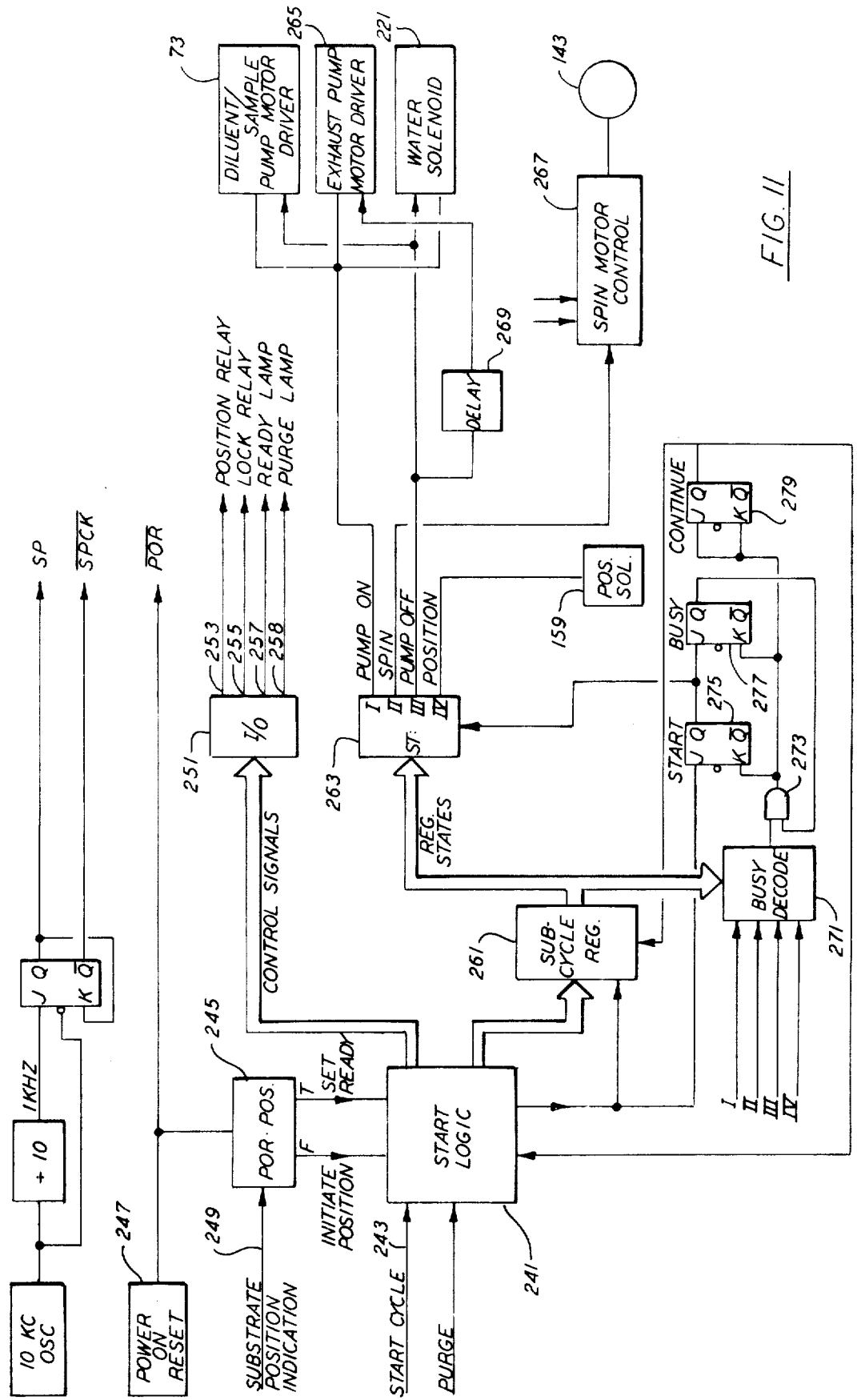
FIG. 11 is a block-logic diagram for the apparatus of FIG. 1.

FIG. 11, a basic block-logic diagram of the control system for the spinner, is essentially an implementation of the flow diagram of FIG. 2 utilizing standard logic-building blocks similar to those used for the probe control.

Operation of the system requires appropriate signal inputs to a start logic network 241. In addition to a signal from the operator on line 243, start logic receives inputs from a logic block 245 indicating the status of parameters determining whether or not the system is ready to start, e.g., angular position of the spinner, position of the carriage. To this end, block 245 receives a signal from a "power-on" reset module 247 and, via line 249, an indication of the substrate holder position from the microswitch of FIG. 7. When starting initially, it is important that the substrate holder be properly aligned so that the carriage can be retracted from the centrifuge chamber. Thus, depending on these inputs, a command is given either to initiate position, i.e., to position the centrifuge motor 143 of FIG. 7 so that the coupling notch is properly aligned or to set the ready light if that has already been done. These outputs are provided from logic block 245, which will contain necessary logic gates for the purpose, to start logic block 241.

Then, when receiving an input from the operator on line 243, start logic 241 provides a number of control signal outputs through an input/output block 251: (1) on line 253, a signal to engage the position relay or solenoid 159; (2) on line 255, a signal to de-energize carriage locking solenoid 169; and (3) on lines 257 and 258, signals to control the ready lamp and purge lamp indicating whether or not a cycle is in progress or ready to start. In the condition just mentioned, where the cycle has been started, the ready lamp will, of course, be extinguished. Start logic 241 also provides a signal to a subcycle register 261, which operates much in the manner of the subcycle register (97, FIG. 6) of the probe control system to carry out the various subcycles indicated in FIG. 2. The output from subcycle register 261 is provided to a cycle register 263 which provides four different outputs designated I, II, III and IV:

I. The first output, which corresponds to block 43 of FIG. 2, provides an input to a pump motor driver 73, to a driver 265 for the drain pump motor 227 of FIG. 10, and to the water solenoid valve 221.

II. The register then steps to the next function, which corresponds to block 45 of FIG. 2, to carry out the spin program. This output is provided to a spin motor control block 267 which includes conventional integrating means for accelerating and decelerating the motor. The motor is accelerated to a speed of approximately 35 rpm, maintained at that speed for a short time, and decelerated.

III. Once the spin cycle is carried out, register 263 steps to the "pump-off" output, represented by block 47 on FIG. 2. This output is utilized directly to turn off the water solenoid and, through a delay 269, to terminate the exhaust pump drive to get the four second delay mentioned above.

IV. In the last register step, the position cycle is carried out in which an output to de-energize the solenoid 159 so that the centrifuge motor, which is now rotating slowly will be stopped in the requisite position to enable retraction of substrate carriage.

During the various operations I, II, III and IV, indications are fed back to a "busy decode" module 271 which is coupled through an AND gate 273 to three flip-flops 275, 277 and 279 which are used to step subcycle register 261 and concomitantly, cycle register 263 through the various steps. As the inputs to the busy decode module correspond to the outputs of cycle register 263, in each case at the beginning of a particular step the start flip-flop is set to advance the register 263. As long as this step is being carried out, an output from busy decode 271 prevents starting another cycle. However, once the cycle is completed, the busy flip-flop is reset and the program can continue in accordance with an output from the continue flip-flop. This ensures that a subsequent step is not started while a previous step is in progress.

Thus, an improved spinner for preparing blood smears on slides has been shown. Although specific embodiments have been illustrated and described, it will be obvious to those skilled in the art that various modifications may be made without departing from the spirit of the invention, which is intended to be limited solely by appended claims.

What is claimed is:

1. A method of preparing a blood film on a planar substrate comprising the steps of:
   depositing a blood specimen on a substrate;
   spinning the substrate at a high angular rate about an axis perpendicular to its plane; and
   surrounding the substrate with a flowing curtain of liquid positioned to intercept and collect blood particles and aerosols spun off the substrate.

2. A method according to claim 1 including the further step of continuously directing the liquid from said curtain into a waste line during the spinning of said substrate.

3. A method according to claim 2 wherein the spinning is carried on in an enclosed chamber from which said liquid is pumped and including the further step of terminating the liquid curtain flow while continuing to pump the liquid from the enclosed chamber to form a partial vacuum therein tending to remove any residual blood in aerosol form.

4. A method according to claim 3 wherein the blood specimen is diluted before being deposited on the substrate.

5. A method according to claim 4 wherein dilution is in a ratio of 2 parts blood to 1 part diluent and the diluent is physiological saline solution.

6. A method according to claim 5 wherein the substrate is spun at a speed in the range of 3000 and 4000 rpm.

7. A method according to claim 6 wherein the substrate is spun at 3500 rpm.

8. A method according to claim 4 wherein said dilution is effected by steps comprising:
   a. drawing a blood specimen into an aspirating probe; and
   b. discharging said specimen in a measured amount along with a measured amount of diluent from said probe.

9. A method according to claim 8 including the further step of mixing said specimen and diluent in the tip of said probe before discharging.

* * * * *